United States Patent [19]

Li

[11] Patent Number: 4,661,444

[45] Date of Patent: * Apr. 28, 1987

[54] HOMOGENEOUS IMMUNOASSAYS EMPLOYING DOUBLE ANTIBODY CONJUGATES COMPRISING ANTI-IDIOTYPE ANTIBODY

[75] Inventor: Conan K. N. Li, Allston, Mass.

[73] Assignee: Ortho Diagnostic Systems Inc., Raritan, N.J.

[*] Notice: The portion of the term of this patent subsequent to Feb. 21, 2001 has been disclaimed.

[21] Appl. No.: 594,164

[22] Filed: Mar. 29, 1984

[51] Int. Cl.$^4$ .................. G01N 33/53; G01N 33/566; G01N 33/543; G01N 33/551

[52] U.S. Cl. .......................................... 435/7; 435/12; 435/21; 435/28; 436/501; 436/518; 436/524; 436/528; 436/540; 436/800

[58] Field of Search ................. 435/7, 12, 21, 28; 436/501, 518, 524, 527, 528, 531, 532–534, 540, 546, 800

[56] References Cited

U.S. PATENT DOCUMENTS 4,433,059  2/1984  Chang et al. .................. 436/512

Primary Examiner—Sidney Marantz
Assistant Examiner—Patricia L. DeSantis
Attorney, Agent, or Firm—Mark A. Hofer

[57] ABSTRACT

Homogeneous immunoassays employing double ligand binding conjugates comprising an anti-idiotype binding partner. The anti-idiotype binding partner competes with ligand for an insolubilized ligand specific binding partner. Inhibition of binding of the conjugate to the insolubilized binding partner due to ligand binding permits the second binding partner in the conjugate to bind with insolubilized label means. Thus, detection of label is inversely related to the presence of ligand in the sample.

13 Claims, 6 Drawing Figures

LIGAND PRESENT

LIGAND PRESENT

LIGAND ABSENT

LIGAND PRESENT

LIGAND ABSENT

LIGAND PRESENT

LIGAND ABSENT

HOMOGENEOUS IMMUNOASSAYS EMPLOYING DOUBLE ANTIBODY CONJUGATES COMPRISING ANTI-IDIOTYPE ANTIBODY

FIELD OF THE INVENTION

This invention relates generally to immunoassays useful for detecting soluble substances or ligands such as antigens and more specifically, relates to homogeneous assays relying upon a double antibody conjugate which competes with antigen for an immobilized binding site.

The detection of specified antigens (defined as a substance whose introduction into an animal stimulates the production of antibodies capable of reacting specifically therewith), haptens (a substance requiring additional accessory materials before its introduction into an animal stimulates the production of antibodies specific therefor), and the like substances (hereinafter collectively referred to as "ligands") in body fluids such as blood, sputum, urine, and the like has in recent years become of utmost importance in both the research and clinical enviroments. The detection of such ligands can often be related to various disease states and consequently, is of extreme usefulness in diagnosis as well as gaining basic understandings concerning the genesis of disease as well as monitoring the effectiveness of therapies therefor.

Accordingly, improved methods for detecting ligands in aqueous samples are constantly sought. In particular, such methods or assays are typically characterized by their speed and facility of employment, as well as by their sensitivity. Preferred assays are those requiring less effort to perform in shorter time periods and characterized by greater sensitivity.

Immunoassays in general are based upon the immunological reaction between proteins such as antibodies, antibody fragments, or even artificially generated peptides (hereinafter collectively referred to as "ligand binding partners") and the substance for which they are specific, i.e., the ligands. Immunological reactions are generally characterized by their high specificity and accordingly, numerous schemes have been developed in order to take advantage of this characteristic. Typically, such schemes require either purified antigen or ligand to compete with the ligand being measured, and a labeled and immobilized ligand binding partner; or multiple immobilized and labeled ligand binding partners reactive with themselves and the ligand.

Those techniques which require purified ligand to compete with sample ligand for the binding site on the ligand binding partner disadvantageously entail difficult and expensive manufacturing processes in order to produce the purified ligand in a form that is sufficiently intact to permit linkage with its specific binding partner. The production difficulties are exacerbated with ligands which are small and generally uncharacterized.

It is an object of the present invention to provide a competitive type of assay which does not, however, rely upon competition of sample ligand with purified ligand, thus obviating many of the otherwise difficult and expensive manufacturing processes heretofore associated with the production of purified intact ligand.

In one class of assays known as inhomogeneous assays, the sample containing the substance to be detected (ligand) is mixed with some of the assay reactants and, after permitting the immunological reactions to occur, the resultant constituents are separated into soluble and insoluble phases. One or the other of these phases is subsequently analyzed for the presence of detectable label permitting conclusions to be made regarding the presence of ligand in the sample. Such inhomogeneous assays disadvantageously require separation and washing steps in order to obtain the two phases, as well as accessory materials and apparatus to accomplish same.

It is another object of the present invention to avoid such disadvantages typically associated with inhomogeneous assays by providing a homogeneous immunoassay which does not require a separation step prior to detection of the label.

Nussenzweig et al. described in Science, 215:1637–1639 (1982) a competitive solid phase radioimmunoassay method which does not rely upon competition of the sample antigen with a purified, investigator supplied antigen reagent. Instead, Nussenzweig describes the use of an anti-idiotype antibody. An idiotype may be defined as an individually specific antigenic determinant associated with a particular type of antibody but not with other members of the general antibody class and for which an antibody can be raised capable of specifically reacting with the idiotype. For instance, the idiotype is generally thought of as associated with the variable region of an antibody and may comprise whole or part of the antigen binding site. In contrast, allotypic determinants are determinants commonly associated with all members of the antibody class, and would include, for instance, the Fc portions or nonvariable regions of antibodies. Anti-idiotype binding partners, like antibodies in general, are typically easier to produce and purify than are the ligands which can compete with such anti-idiotypes for binding sites on the ligand binding partner. Hence, production techniques for anti-idiotype antibodies typically avoid the problems associated with purified intact ligand production.

It is yet another object of the present invention to utilize an anti-idiotype antibody approach to thereby benefit from the value that such ligand binding partners may provide.

Heretofore, anti-idiotype antibodies have been generally used for investigations of immune functions and how such systems can break down creating autoimmune diseases. References regarding these aspects as well as general production techniques are fully incorporated herein by reference and include the following: Brient et al., Quantitative Investigations of Idiotypic Antibodies, J. Exp. Med., 132:951–962 (1970); Geha et al., Anti-idiotypic Antisera in Man, J. Immunology, 121, 4:1518–1523 (1978); and Rauch et al., A High Frequency Idiotypic Marker of Anti-DNA Autoantibodies and MRL-Ipr/Ipr Mice, J. Immunology, Vol. 129, 1:236–241 (1982).

It is still another object of the present invention to provide new methods of using anti-idiotype antibodies or binding partners in immunoassays thereby greatly expanding the utility of such binding partners.

In a related patent application of Chang et al. entitled "Double Antibody Conjugate" (U.S. Ser. No. 299,764, now U.S. Pat. No. 4,433,059), there are described novel reagents comprising two antibodies covalently coupled tail to tail whereby each antibody retains substantially all of its reactivity. The two antibodies have differing specificities and accordingly, can be directed against either of two different ligands. The methods for making such a conjugate are fully disclosed in the Chang et al. U.S. Pat. No. 4,433,059 and hereby fully incorporated by reference.

It is still yet another object of the present invention to incorporate the concept of a double ligand binding partner such as the Chang et al. concept in conjunction with an anti-idiotype ligand binding partner into a homogeneous assay format.

All immunoassays have, as a common characteristic, the requirement that the immunological reaction be somehow monitorable. Typically, monitoring may be accomplished by associating with either (1) the ligand for which the ligand binding partner is specific or (2) the ligand binding partner itself, a label which may be readily detected in either the aqueous or solid phases. Such labels may include, for instance, fluorophores, phosphorescent molecules, chemiluminescent molecules, radioisotopes, enzymes, reflective particles and the like. Although all of these labels and the technology associated with their detection have, in recent years, become highly developed, one prerequisite often necessitated to their detection is the removal of the labeled constituent which has not participated in the immunological reaction.

It is a still yet further object of the present invention to provide methods whereby the label need not be removed from the soluble phase prior to its detection thereby simplifying the procedural steps associated with prior methods.

BRIEF SUMMARY OF THE INVENTION

In accordance with the principles and objects of the present invention, there are provided immunoassays which employ a double ligand binding partner conjugate wherein one of the ligand binding partners is an anti-idiotype binding partner. The immunoassay further comprises an insolubilized binding partner specific for the ligand to be detected and for the anti-idiotype binding partner. Binding of the ligand to the insolubilized ligand binding partner prevents immunological reaction of the insolubilized binding partner with the anti-idiotype binding partner end of the double binding partner conjugate and vice versa.

In the preferred format of the immunoassay of the instant invention, the foregoing materials are permitted to immunologically react and, in a subsequent step, an insolubilized detectable label is added to the soluble phase. The nonidiotype portion of the double ligand binding partner conjugate is preferably selected to be specific for this insolubilized label such that immunological reaction therebetween results in significant alteration of label detectability. In the most preferred form, such a label may, for instance, be an enzyme which normally would convert a colorless substrate to an easily detectable colored product. The nonidiotype ligand binding partner of the double ligand binding conjugate is preferably selected to be specific for the enzyme whereby enzymatic activity may be blocked upon immunological reaction. Thus, the presence of ligand in the sample may be inversely related to the level of enzymatic activity or product detectable.

BRIEF DESCRIPTION OF THE DRAWINGS

Further understanding of the instant invention as well as recognition of the associated principles may be had by reference to the drawings wherein.

DETAILED DESCRIPTION OF THE DRAWINGS AND BEST MODE

A generalized schematic description of the principles of the present invention are shown in the accompanying figures which illustrate the operation of the instant invention in the two possible extremes: overwhelming ligand presence and complete ligand absence in the sample. It should be readily appreciated that the principles will hold for other situations intermediate these extremes and, that the reagents are depicted in a purely schematic form in order to facilitate understanding rather than to provide accurate descriptions of molecular shapes, orientations and the like.

Figure 1A:
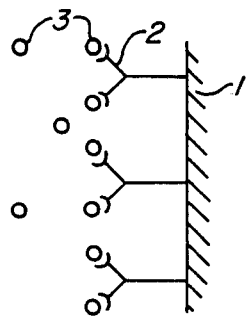
FIGS. 1a–1c schematically depict operation of the immunoassay given a sample having ligand present.
Figure 2A:
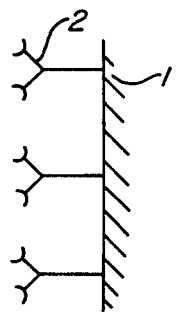
FIGS. 2a–2c schematically illustrate the principles of the instant invention given a sample having an absence of ligand to be detected.

Beginning first with FIGS. 1a and 2a, there are shown ligand binding partners 2 insolubilized upon a surface 1 and specific for ligand 3. Such surfaces could take on a variety of formats and include, for instance, latex beads, also sometimes referred to as microparticles although this is a more extensive group since beads or particles may be formed from a variety of other materials, larger sized beads such as macroparticles, plastic and glass surfaces such as the walls of a test tube or microtiter tray, as well as other types of surfaces including those formed from porous plastic or other types of membranes. These various types of surfaces, and the methods of attaching immunoglobulin or pieces thereof (such as Fab or F(ab')$_2$ portions thereof) to the respective insoluble surfaces are well-known to those skilled in the art. Such attachment techniques would include, for instance, nonspecific absorption, attachment with protein A (from Staphylococcus aureus), attachment using avidin-biotin, and chemical covalent attachment techniques.

In the preferred procedure of the instant invention, the sample containing the ligand to be analyzed 3 is contacted with the insolubilized ligand binding partner 2 under conditions permitting an immunological reaction therebetween to occur. FIG. 1a demonstrates how an excess of ligand would occupy the available, relevant binding sites. Thereafter, the double ligand binding partner conjugate complex 15 (alternately referred to herein as either the double antibody conjugate or conjugate complex) is added under conditions conducive to further immunological reaction.

The double antibody conjugate 15 comprises two ligand binding partners or fragments thereof such as Fab or F(ab')$_2$ portions depending upon the mode of conjugation. Specifically, the conjugate complex 15 comprises in its most preferred form, two ligand binding partners having differing specificities wherein one of the ligand binding partners 10, is an anti-idiotype binding partner specific for the ligand binding site on the insolubilized ligand binding partner 2. Thus, the anti-idiotype ligand binding partner 10 is capable of competing with ligand 3 for the binding site on insolubilized ligand binding partner 2. It should be noted, however, that the ligand binding partner 10, need not react identically with the insolubilized binding partner 2 as does ligand 3 but merely react in such manner as to prohibit or block subsequent binding of the ligand 3. Similarly, the anti-idiotype ligand binding partner itself will be immunologically blocked by the prior immunological reaction of ligand 3 with binding partner 2.

It should be noted, the present invention is not limited to the use of anti-idiotype ligand binding partners but, also contemplates those binding partner variations which act in a manner similar to the basic blocking function of the anti-idiotype immunoglobulin. Specifically, anti-framework binding partners or antibodies, antibody fragments, and artificially produced peptide analogs are also contemplated. Anti-framework antibodies are generally understood to refer to those immunoglobulins which react with only a portion of the binding site on the binding partner 2 or react with no portion of the binding site but instead, with the so-called framework or contiguous structure associated with or next to the binding site. Thus, the anti-framework binding partner, although not binding directly with the ligand binding site, prevents the binding of the ligand because of steric hindrance or other protein confirmational changes associated with its binding. It is the possibility of providing such anti-idiotype, anti-framework, antibody fragments or the like binding partners in the conjugate complex 15 that provides versatility and flexibility of reagent production without substantial deviation from the desired results. Derivation of anti-idiotype binding partners and the like may be had to a variety of references including an article by Andrzejewski et al., Antigen Binding Diversity and Idiotypic Cross-Reactions Among Hybridoma Autoantibodies to DNA, Journal of Immunology, Vol. 126, 1:226-231, the relevant portions of which are hereby incorporated by reference.

Figure 1B:
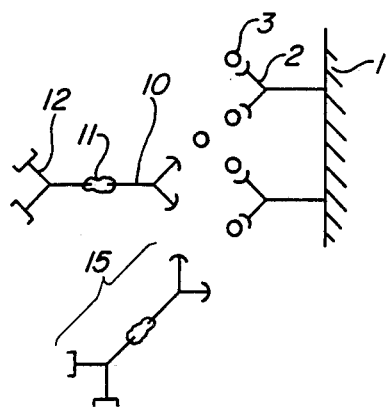
Figure 2B:
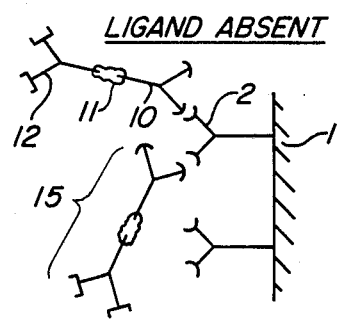
Figure 1C:
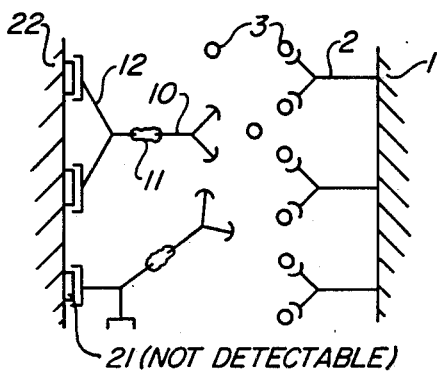
Figure 2C:
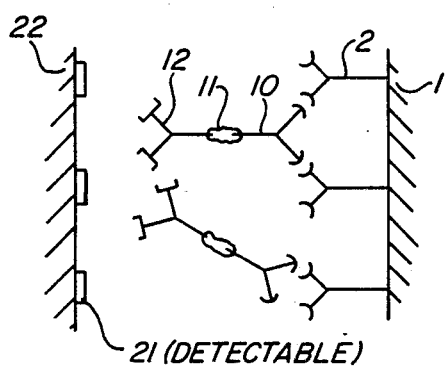

With further reference to FIGS. 1b and 2b, the conjugate complex 15 further comprises a second ligand binding partner 12 linked to the anti-idiotype binding partner 10 through linkage 11. Linkage 11 has been graphically depicted as a separate structure and may, in certain circumstances so exist depending upon the type of conjugation technique employed. As previously intimated, a variety of techniques are available for formulating such a conjugate complex including, for instance, the reoxidization of Fab' fragments of the binding partners 10 and 12. Additional details may be available by reference to Fudenberg et al., "Serologic Demonstration of Dual Specificity of Rabbit Bivalent Hybrid Antibody", J. Exp. Medicine, 119:151-166 (1964). Another well-known technique for coupling immunoglobulins via their Fc portions relies upon their mutual attachment to protein A. Still yet another method for formulating the conjugate complex 15 is described in the Chang et al. application referred to earlier and also incorporated herein by reference.

Thus, as depicted in FIG. 1b, the presence of ligand in the sample 3 blocks the binding site on binding partner 2 thereby preventing immunological reaction between the anti-idiotype binding partner 10 and the insolubilized binding partner 2. Conversely, absence of the ligand permits immunological reaction as shown in FIG. 2b. As will be readily appreciated, appropriate temperature, pH, concentration and the like conditions are preferably provided in order to optimize immunological reactivity and, ultimately sensitivity. Further, it may be appreciated that as an alternative to performing the assay in the preferred sequential steps outlined above, the foregoing may be accomplished in one simultaneous operation.

Following the foregoing reactions, label 21 insolubilized upon a solid phase surface 22 is added. The insoluble surface 22 is preferably of a configuration which presents detectable label 21 to conjugate complex 15 but at a distance sufficiently large so that the ligand binding partner 12, specific for the detectable label 21, cannot react with label 21 if anti-idiotype ligand binding partner 10 has previously (or simultaneously) reacted with insolubilized binding partner 2. Thus, this distance may be dependent in part upon the linkage method or substance 11 employed in formulating conjugate complex 15. One suitable arrangement contemplated is the attachment of the insolubilized binding partner 2 onto the walls of a microtiter tray 1 and the subsequent insertion of paddle or the like insert means 22 having detectable label 21 attached thereto. Clearly, innumerable physical alternatives abound and will be readily appreciated by those skilled in the art.

Detectable label 21, can similarly take on a variety of forms including fluorescent, chemiluminescent and phosphorescent molecules whose respective spectral characteristics are significantly altered upon immunological reaction with binding partner 12. Still other labels are possible and include reflective particles, and other light scattering materials. Such particles have found widespread use in a variety of flow cytometric methods which characterize particles on the basis of associated labels which present various fluorescent and light scattering characteristics.

In the most preferred mode, the detectable particle 21 will comprise an enzyme whose enzymatic activity is significantly altered, or preferably, completely blocked by its immunological reaction with the second binding partner 12. Thus, the activity of such an enzyme may be readily detected or determined by adding to the aforementioned immunoassay components, a substrate which is enzymatically converted into a detectable product. This is a well-known technique associated with the so-called ELISA techniques and a variety of enzyme, substrate, product systems are readily available. For instance, the enzyme may be an alkaline phosphatase which acts on p-nitrophenyl phosphate to produce p-nitrophenol whose increasing presence is detected by light extinction. Alternatively, the same enzyme may be used to convert 4-methylumbelliferyl phosphate into 4-methylumbelliferone which may be readily detected fluorimetrically. Still another example includes urease, which reacts upon urea, preferably provided substantially free of ammonia, to produce ammonia and other products. Presence of ammonia may be readily detected by the alteration of pH. pH changes can, of course, be readily detected by using gas permeable membrane covered electrodes, glass electrodes, or insulated gate field effect transistors such as those described in the Chemfet pioneering work by Janata et al. at the Universisty of Utah.

The methods for producing ligand binding partners specific for the ligands, the ligand binding sites and the detectable labels as required by the instant invention, are generally well-known, particularly with respect to antibodies of polyclonal origin. Polyclonal antibodies may be used in the instant invention, however, in most cases the so-called monoclonal antibodies will be preferred in order to maximize sensitivity, facilitate ease of production and to minimize nonspecific reactivities. Pursuant to the hybridoma generation principles and methods described by Kohler and Milstein (Nature, Vol. 256:495, 1975) and others, the production of monoclonal antibodies, their selection and characterization has also become standard practice. By employing a thusly generated ligand specific binding partner 2 as the immunizing substance, anti-idiotype, anti-framework and the like binding partners 10 may also be readily produced. For example, the production of anti-idiotype anti-arsenate antibodies is described by Kuettner et al., Quantitative Investigation of Idiotypic Antibodies VI, Idiotypic Specificity as a Potential Genetic Marker for the Variable Regions of Mouse Immunoglobulin Polypeptide Chains, J. Exp. Med., 135:579 (1972). It will be readily apparent that the procedures described therein, and incorporated herein by reference, can be suitably modified to readily permit the production of virtually any anti-idiotype or similar antibody. Likewise, antibodies may be raised by using only critical peptide sequences instead of the whole protein as these sequences may, in some circumstances be more easily produced under controlled conditions.

Thus, in the described format, the instant invention may be used to qualitatively detect the presence of ligand in a sample based on the inverse relationship between the presence of ligand and the labels' detectable characteristic. It will thus be readily apparent that by providing suitable controls against which sample results may be compared, one may employ the methods and logic of the instant invention to also quantitatively detect the presence of the ligand if so desired.

It will be readily appreciated that one skilled in the art will realize that a variety of insubstantial alterations, substitutions and the like can be made to the reagents and procedures described herein without departing from the spirit or scope of the instant invention.

What is claimed is:

1. An immunoassay reagent system for detecting a ligand comprising:
   an insolubilized ligand binding partner;
   a double binding partner conjugate comprising an anti-idiotype binding partner, capable of blocking said ligand from binding with said insolubilized ligand binding partner, coupled to a second binding partner; and
   insolubilized label means for which said second binding partner is specific.

2. The immunoassay reagent system as provided in claim 1 wherein said label means is selected from the group of labels having a characteristic spectral emission consisting of fluorescent molecules, phosphorescent molecules, and chemiluminescent molecules and wherein binding of the second binding partner to said label means results in a detectable change of said label's characteristic spectral emission.

3. The immunoassay reagent system as provided in claim 1 wherein said label means is an enzyme whose activity upon a substrate to produce a detectable product is altered upon binding of the second binding partner to said enzyme.

4. The immunoassay reagent system as provided in claim 3 wherein said enzyme is alkaline phosphatase, said substrate is p-nitrophenyl phosphate, and said product is p-nitrophenol.

5. The immunoassay reagent system as provided in claim 3 wherein said enzyme is alkaline phosphatase, said substrate is 4-methylumbelliferyl phosphate, and said product is 4-methylunbelliferone.

6. The immunoassay reagent system as provided in claim 3 wherein said enzyme is urease, said substrate is substantially ammonia free urea, and said product is ammonia.

7. A method for detecting a ligand in an aqueous sample comprising the steps of:
   (a) contacting said sample suspected of containing the ligand to be detected with an insolubilized ligand binding partner specific for said ligand;
   (b) adding to said sample a double binding partner conjugate comprising a first binding partner of first specificity coupled to a second binding partner of second specificity each binding partner being immunologically reactive, and wherein said first binding partner is an anti-idiotype or anti-framework binding partner specific for said insolubilized ligand binding partner whereby the binding of either said ligand or said first binding partner to said insolubilized binding partner blocks the binding of said first binding partner or said ligand respectively;
   (c) contacting said sample with support means having label means attached thereto, said second binding partner being specific for said label means whereby binding of said second binding partner to said label means alters a detectable characteristic of said label means, said support means being maintained at a distance sufficiently large from said immobilized binding partner to substantially prohibit simultaneous binding of said binding partner conjugate to both said insolubilized binding partner and said label means;
   (d) detecting said detectable characteristic of label means and relative same to the presence of said ligand to be detected.

8. The method as provided in claim 7 wherein said label means is selected from the group consisting of fluorescent molecules, phosphorescent molecules, chemiluminescent molecules and light scattering particles whereby immunological reaction between said second binding partner and said label means results in alteration of detectable spectral characteristics associated with said label means.

9. The method as provided in claim 7 wherein said label means is an enzyme whose capability to produce detectable product from a substrate added to the sample is altered upon immunological reaction between said enzyme and said second binding partner.

10. The method as provided in claim 9 wherein said enzyme is alkaline phosphatase, said substrate is p-nitrophenyl phosphate, and the detecting step comprises detecting increasing light extinction based on increasing levels of the product p-nitrophenyl.

11. The method as provided in claim 9 wherein said enzyme is alkaline phosphatase, said substrate is 4-methylumbelliferyl phosphate, and the detecting step comprises detecting the presence of 4-methylumbelliferone fluorimetrically.

12. The method as provided in claim 9 wherein said enzyme is urease, said substrate is substantially ammonia free urea, and the detecting step comprises detecting pH changes associated with the presence of the product ammonia.

13. In homogeneous immunoassays employing insolubilized binding partners for the detection of ligands in an aqueous sample, the improvement comprising:
   utilizing a double binding partner conjugate to compete with said ligand for said insolubilized binding partner and specific for insolubilized label means.

* * * * *

UNITED STATES PATENT AND TRADEMARK OFFICE
CERTIFICATE OF CORRECTION

PATENT NO. : 4,661,444
DATED      : April 28, 1987
INVENTOR(S) : Conan K. N. Li

It is certified that error appears in the above-identified patent and that said Letters Patent is hereby corrected as shown below:

Col. 8, line 30: "relative" should be --relating--.

Signed and Sealed this

Nineteenth Day of July, 1988

*Attest:*

DONALD J. QUIGG

*Attesting Officer*    *Commissioner of Patents and Trademarks*